(12) United States Patent
Alarcon Heredia et al.

(10) Patent No.: US 11,707,354 B2
(45) Date of Patent: Jul. 25, 2023

(54) METHODS AND APPARATUSES TO INCREASE INTRAOCULAR LENSES POSITIONAL STABILITY

(71) Applicant: AMO Groningen B.V., Groningen (NL)

(72) Inventors: Aixa Alarcon Heredia, Groningen (NL); Bram Koopman, Groningen (NL); Marrie Van Der Mooren, Engelbert (NL); Robert Rosén, Groningen (NL); Jacolien Graver, Groningen (NL); Selma Boersma, Groningen (NL); Luuk Franssen, Groningen (NL); John Van Den Berg, Noordwijk (NL)

(73) Assignee: AMO Groningen B.V., Groningen (NL)

( * ) Notice: Subject to any disclaimer, the term of this patent is extended or adjusted under 35 U.S.C. 154(b) by 549 days.

(21) Appl. No.: 16/128,434

(22) Filed: Sep. 11, 2018

(65) Prior Publication Data

US 2019/0076241 A1 Mar. 14, 2019

Related U.S. Application Data

(60) Provisional application No. 62/556,853, filed on Sep. 11, 2017.

(51) Int. Cl.
*A61F 2/16* (2006.01)
*A61F 9/008* (2006.01)

(52) U.S. Cl.
CPC .......... *A61F 2/1648* (2013.01); *A61F 2/1618* (2013.01); *A61F 2/1624* (2013.01);
(Continued)

(58) Field of Classification Search
CPC .... A61F 2/1648; A61F 2/1618; A61F 2/1624; A61F 2/1637; A61F 2/1662;
(Continued)

(56) References Cited

U.S. PATENT DOCUMENTS

| 1,483,509 A | 2/1924 | Bugbee |
| 2,129,305 A | 9/1938 | William |

(Continued)

FOREIGN PATENT DOCUMENTS

| AU | 3225789 A1 | 10/1989 |
| CA | 3002085 A1 | 5/2017 |

(Continued)

OTHER PUBLICATIONS

International Search Report and Written Opinion for Application No. PCT/EP2018/074496, dated Dec. 21, 2018, 17 pages.

(Continued)

*Primary Examiner* — Anh T Dang
(74) *Attorney, Agent, or Firm* — Johnson & Johnson Surgical Vision, Inc.

(57) ABSTRACT

A multi-piece IOL assembly is provided that includes a platform and an optic. The platform has an inner periphery surrounding an inner zone of the platform. The optic has an optical zone, an outer periphery and a retention mechanism disposed on the outer periphery. The optic is configured to be disposed in the inner zone of the platform and to extend to a location between the inner periphery and the outer periphery of the platform to be secured to the platform at the location. The platform can be secured to an inner periphery of the eye or can be formed into a natural lens by cutting the lens using a laser or other energy source.

24 Claims, 9 Drawing Sheets

(52) U.S. Cl.
CPC .......... *A61F 2/1637* (2013.01); *A61F 2/1662* (2013.01); *A61F 9/00834* (2013.01); *A61F 2/1602* (2013.01); *A61F 2/1632* (2013.01); *A61F 2/1645* (2015.04); *A61F 2002/169* (2015.04); *A61F 2002/1682* (2015.04); *A61F 2002/1696* (2015.04); *A61F 2002/16901* (2015.04); *A61F 2002/16965* (2015.04); *A61F 2009/0087* (2013.01); *A61F 2250/0062* (2013.01); *A61F 2250/0097* (2013.01)

(58) Field of Classification Search
CPC .... A61F 2/1602; A61F 2/1645; A61F 2/1632; A61F 9/00834; A61F 2002/16965; A61F 2002/16901; A61F 2002/1696; A61F 2250/0097
See application file for complete search history.

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | Carle |
| 3,210,894 A | 10/1965 | Bentley et al. |
| 3,222,432 A | 12/1965 | Grandperret |
| 3,227,507 A | 1/1966 | William |
| 3,305,294 A | 2/1967 | Alvarez |
| 3,339,997 A | 9/1967 | Wesley |
| 3,415,597 A | 12/1968 | Willard |
| 3,420,006 A | 1/1969 | Howard |
| 3,431,327 A | 3/1969 | George |
| 3,482,906 A | 12/1969 | David |
| 3,507,565 A | 4/1970 | Luis et al. |
| 3,542,461 A | 11/1970 | Louis et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen et al. |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen et al. |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |

(56) References Cited

U.S. PATENT DOCUMENTS

| | | |
|---|---|---|
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,833,890 A | 5/1989 | Kelman |
| 4,834,749 A | 5/1989 | Orlosky |
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Msser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk et al. |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barre et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barre et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |

(56) References Cited

U.S. PATENT DOCUMENTS

| | | |
|---|---|---|
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A * | 9/1998 | Eggleston ............ A61F 2/1613 623/6.39 |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skottun et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,797,004 B1 | 9/2004 | Brady et al. |
| 6,818,017 B1 | 11/2004 | Shu |
| 6,818,158 B2 | 11/2004 | Pham et al. |
| 6,827,738 B2 | 12/2004 | Willis et al. |

(56) References Cited

U.S. PATENT DOCUMENTS

| | | |
|---|---|---|
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,942,695 B1 | 9/2005 | Chapoy et al. |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,276,544 B2 | 10/2007 | Lai et al. |
| 7,344,617 B2 | 3/2008 | Dubrow |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 9,095,424 B2 | 8/2015 | Kahook et al. |
| 9,358,103 B1 | 6/2016 | Wortz et al. |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0103536 A1 | 8/2002 | Landreville et al. |
| 2002/0120329 A1 | 8/2002 | Lang et al. |
| 2002/0151973 A1 | 10/2002 | Arita et al. |
| 2002/0161434 A1 | 10/2002 | Laguette et al. |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 | 6/2003 | Glazier |
| 2003/0109925 A1 | 6/2003 | Ghazizadeh et al. |
| 2003/0114927 A1 | 6/2003 | Nagamoto |
| 2003/0130732 A1 | 7/2003 | Sarfarazi |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee |
| 2004/0039446 A1 | 2/2004 | McNicholas |
| 2004/0082993 A1 | 4/2004 | Woods |
| 2004/0082995 A1 | 4/2004 | Woods |
| 2004/0106992 A1 | 6/2004 | Lang et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0069432 A1* | 3/2006 | Tran .............. A61F 2/1629 623/6.41 |
| 2006/0095127 A1 | 5/2006 | Feingold et al. |
| 2006/0098162 A1 | 5/2006 | Bandhauer et al. |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0032866 A1 | 2/2007 | Portney |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1 | 6/2007 | Klima |

(56) References Cited

U.S. PATENT DOCUMENTS

| | | |
|---|---|---|
| 2007/0156236 A1 | 7/2007 | Stenger |
| 2007/0213817 A1 | 9/2007 | Esch et al. |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2008/0300680 A1 | 12/2008 | Joshua |
| 2009/0012609 A1 | 1/2009 | Geraghty et al. |
| 2009/0234448 A1 | 9/2009 | Weeber et al. |
| 2010/0057203 A1 | 3/2010 | Glick et al. |
| 2010/0228346 A1 | 9/2010 | Esch |
| 2011/0029074 A1 | 2/2011 | Reisin et al. |
| 2011/0035001 A1 | 2/2011 | Woods |
| 2012/0046744 A1 | 2/2012 | Woods et al. |
| 2015/0250583 A1 | 9/2015 | Rosen et al. |
| 2015/0320547 A1 | 11/2015 | Rosen et al. |

FOREIGN PATENT DOCUMENTS

| | | |
|---|---|---|
| CH | 681687 A5 | 5/1993 |
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 0162573 A2 | 11/1985 |
| EP | 212616 A2 | 3/1987 |
| EP | 246216 A2 | 11/1987 |
| EP | 328117 A2 | 8/1989 |
| EP | 0329981 A1 | 8/1989 |
| EP | 331457 A2 | 9/1989 |
| EP | 336877 A1 | 10/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 779063 A1 | 6/1997 |
| EP | 0780718 A1 | 6/1997 |
| EP | 0897702 A2 | 2/1999 |
| EP | 766540 B1 | 8/1999 |
| EP | 1108402 A2 | 6/2001 |
| EP | 1321112 A1 | 6/2003 |
| EP | 1647241 A2 | 4/2006 |
| EP | 1424049 B1 | 6/2009 |
| EP | 2629698 B1 | 5/2018 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | H02126847 A | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 8404449 A1 | 11/1984 |
| WO | 8603961 A1 | 7/1986 |
| WO | 8700299 A1 | 1/1987 |
| WO | 8707496 A1 | 12/1987 |
| WO | 8803961 A1 | 6/1988 |
| WO | 8902251 A1 | 3/1989 |
| WO | 8911672 A1 | 11/1989 |
| WO | 8911872 A1 | 12/1989 |
| WO | 9000889 A1 | 2/1990 |
| WO | 9109336 A1 | 6/1991 |
| WO | 9302639 A1 | 2/1993 |
| WO | 9305733 A1 | 4/1993 |
| WO | 9416648 A1 | 8/1994 |
| WO | 9503783 A1 | 2/1995 |
| WO | 9610968 A1 | 4/1996 |
| WO | 9615734 A2 | 5/1996 |
| WO | 9625126 A1 | 8/1996 |
| WO | 9635398 A1 | 11/1996 |
| WO | 9712272 A1 | 4/1997 |
| WO | 9727825 A1 | 8/1997 |
| WO | 9743984 A1 | 11/1997 |
| WO | 9805273 A1 | 2/1998 |
| WO | 9821621 A1 | 5/1998 |
| WO | 9849594 A1 | 11/1998 |
| WO | 9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | 0027315 A1 | 5/2000 |
| WO | 0035379 A1 | 6/2000 |
| WO | 0046629 A1 | 8/2000 |
| WO | 0059407 A1 | 10/2000 |
| WO | 0061036 A1 | 10/2000 |
| WO | 0066037 A1 | 11/2000 |
| WO | 0066039 A1 | 11/2000 |
| WO | 0066040 A1 | 11/2000 |
| WO | 0066041 A1 | 11/2000 |
| WO | 0108605 A1 | 2/2001 |
| WO | 0119288 A1 | 3/2001 |
| WO | 0119289 A1 | 3/2001 |
| WO | 0128144 A1 | 4/2001 |
| WO | 0134061 A1 | 5/2001 |
| WO | 0134066 A1 | 5/2001 |
| WO | 0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |

(56) References Cited

FOREIGN PATENT DOCUMENTS

| | | |
|---|---|---|
| WO | 0219949 A2 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03015657 A2 | 2/2003 |
| WO | 03015669 A1 | 2/2003 |
| WO | 03034949 A2 | 5/2003 |
| WO | 03049646 A2 | 6/2003 |
| WO | 03057081 A2 | 7/2003 |
| WO | 03059196 A2 | 7/2003 |
| WO | 03059208 A2 | 7/2003 |
| WO | 03075810 A1 | 9/2003 |
| WO | 03084441 A1 | 10/2003 |
| WO | 03092552 A1 | 11/2003 |
| WO | 2004000171 A1 | 12/2003 |
| WO | 04020549 A1 | 3/2004 |
| WO | 04037127 A2 | 5/2004 |
| WO | 04073559 A1 | 9/2004 |
| WO | 05011531 A2 | 2/2005 |
| WO | 05018504 A1 | 3/2005 |
| WO | 2005019871 A2 | 3/2005 |
| WO | 03082147 A3 | 8/2005 |
| WO | 05084587 A2 | 9/2005 |
| WO | 2005115278 A1 | 12/2005 |
| WO | 06025726 A1 | 3/2006 |
| WO | 06118452 A1 | 11/2006 |
| WO | 2007040964 A1 | 4/2007 |
| WO | 2007067872 A2 | 6/2007 |
| WO | 2008077795 A2 | 7/2008 |
| WO | 2008079671 A1 | 7/2008 |
| WO | 2008108524 A1 | 9/2008 |
| WO | 2009021327 A1 | 2/2009 |
| WO | 2010093823 A2 | 8/2010 |
| WO | 2016142490 A1 | 9/2016 |
| WO | 2017079449 A1 | 5/2017 |
| WO | 2017096087 A1 | 6/2017 |
| ZA | 8808414 A | 7/1989 |

OTHER PUBLICATIONS

Khng C., et al., "Evaluation of the Relationship between Corneal Diameter and Lens Diameter," Journal of Cataract & Relactive Surgery, Mar. 2008, vol. 34 (3), pp. 475-479.
Lovisolo C.F., et al., "Phakic Intraocular Lenses," Survey of Ophthalmology, Nov.-Dec. 2005, vol. 50 (6), pp. 549-587.
Vass C., et al., "Prediction of Pseudophakic Capsular bag Diameter based on Biometric Variables," Journal of Cataract and Refractive Surgery, Oct. 1999, vol. 25 (10), pp. 1376-1381.
Vogel A., et al., "[Alternatives to Femtosecond Laser Technology: Subnanosecond UV Pulse and Ring Foci for Creation of LASIK Flaps]," Ophthalmology, Jun. 2014, vol. 111 (6), pp. 531-538.
Adler-Grinberg D., "Questioning Our Classical Understanding of Accommodation and Presbyopia," American Journal of Optometry & Physiological Optics, Jul. 1986, vol. 63 (7), pp. 571-580.
Altan-Yaycioglu R., et al., "Pseudo-accommodation with Intraocular Lenses Implanted in the Bag," Journal of Refractive Surgery, May/Jun. 2002, vol. 18 (3), pp. 271-275.
Amo Specs Model AC-21 B, AMO Classic Series, 1992, 1 page.
Chauvin-Opsia, Azurite ACL (0459), 6 pages.
Chiron, Clemente Optfit Model SP525, Brochure Translation, Jul. 12, 1998.
Chrion Vision, Nuvita MA20, 1997, 1 page.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Contact Lens Practice, 1998, pp. 211, 212, 403, 404, 491 and 792.
Fechner P.U., et al., "Iris-Claw Lens In Phakic Eyes to Correct Hyperopia: Preliminary Study," Journal of Cataract and Refractive Surgery, Jan. 1998, vol. 24 (1), pp. 48-56.

Foldable Inliaocular Lens Implants and Small Incision Cataract Surgery, Ohio Valley Eye Physicians, 2004, 4 pages.
Hanita Lenses, Souice Ocular Surgery News International, 1 page.
Hara T., et al., "Accommodative Inliaocular Lens with Spring Action Part 1 Design and Placement in an Excised Animal Eye," Ophthalmic Surgery, Feb. 1990, vol. 21 (2), pp. 128-133.
Hecht E., et al., "Optics", 4th Edition, Addison-Wesley Publishing Company, Feb. 1979, pp. 188-190.
Holladay J.T., et al., "A Three-Part System for Refining Intraocular Lens Power Calculations," Journal of Cataract and Refractive Surgery, Jan. 1988, vol. 14 (1), pp. 17-24.
Holladay J.T., et al., "Analysis of Edge Glare Phenomena in Inliaocular Lens Edge Designs," Journal of Cataract and Refractive Surgery, Jun. 1999, vol. 25 (6), pp. 748-752.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, Jan. 1999, vol. 117 (1), pp. 17-23.
Klien S.A., "Understanding the Diffractive Bifocal Contact Lens," Optometry and Vision Science, Jun. 1993, vol. 70 (6), pp. 439-460.
Kuchle M., et al., "Implantation of a New Accommodative Posterior Chamber Intraocular Lens," Journal of Refractive Surgery, May/Jun. 2002, vol. 18 (3), pp. 208-216.
Lane S.S., et al., "Polysulfone Inliacomeal Lenses," International Ophthalmology Clinics, Winter 1991, vol. 31 (1), pp. 37-46.
Mandell R.B., "Contact Lens Practice", 4th Edition, Charles C. Thomas Publishers, 1988, 11 pages.
Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, May 1, 1990, vol. 1211, pp. 62-66.
McCarey B.E., et al., "Modeling Glucose Distribution in The Cornea," Current Eye Research, Oct. 1990, vol. 9 (11), pp. 1025-1039.
Mediphacos Ltda, Ocular Surgery News International.
Menezo J.L., et al., "Endothelial Study of Iris-Claw Phakic Lens: Four Year Follow-Up," Journal of Cataract Refractive Surgery, Aug. 1998, vol. 24 (8), pp. 1039-1049.
Office Action dated Jul. 19, 2011 for Japanese Application No. 2006526344 filed Sep. 10, 2004.
Opthalmed Inc., OMAC-260.
Pending Claims mailed Jul. 29, 2009 for U.S. Appl. No. 11/618,411, filed Dec. 29, 2006.
Prosecution History for U.S. Appl. No. 11/057,705 (U.S. Appl. No. 11/057,705) filed Feb. 14, 2005.
Prosecution History for U.S. Appl. No. 11/426,888, filed Jun. 27, 2006.
Ramocki J.M., et al., "Foldable Posterior Chamber Intraocular Lens Implantation in the Absence of Capsular and Zonular Support," American Journal of Ophthalmology, Feb. 1999, vol. 127 (2), pp. 213-216.
Simonov A.N., et al., "Cubic Optical Elements for an Accommodative Intraocular Lens," Optics Express, Aug. 2006, vol. 14 (17), pp. 7757-7775.
Storz Opthalmics Inc., Model L122UV ACL.
Taylor B.N., ed., The International System of Units (SI), Aug. 1991, NIST Special Publication 330, 4 pages.
Tetz M., et al., "Evaluating and Defining the Sharpness of Inliaocular Lenses: Part 1: Influence of Optic Design on the Growth of the Lens Epithelial Cells in Vitro," Journal of Cataract and Refiactive Surgery, Nov. 2005, vol. 31 (11), pp. 2172-2179.
Thornton S., "Accommodation in Pseudophakia," in: Percival SPB Color atlas of lens implantation, Chap. 25, St Louis, ed., Mosby, United States, 1991, pp. 159-162.
Universe IOL Center, Ocular Surgery News International.
Video presented by ASCRS Symposium of Cataracts IOL and Refiactive Surgery at the ASOA Congress on Ophthalmic Practice Management. Clinical & Surgical Staff Program on Apr. 10-14, 1999 (VHS Tape).

(56) References Cited

OTHER PUBLICATIONS

World Optics Inc., Ophthalmology Times, Mar. 15, 1995.

* cited by examiner

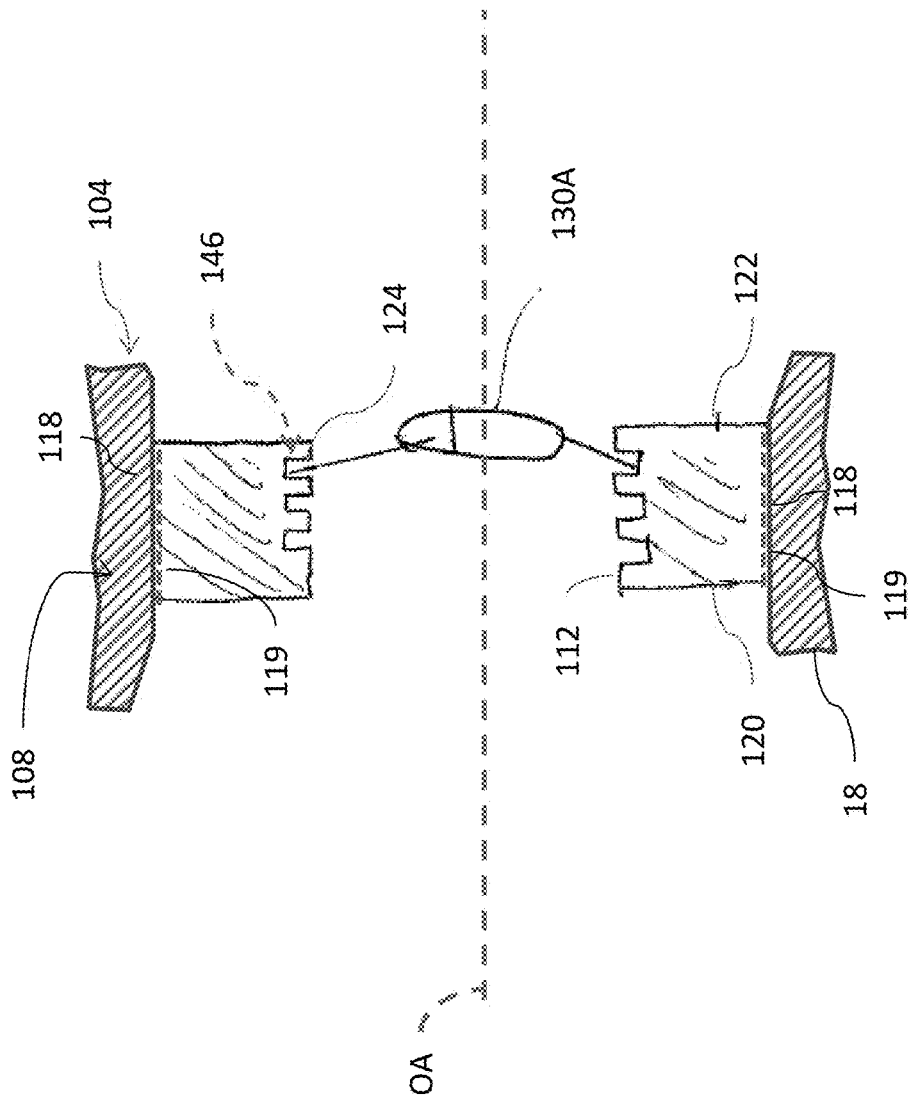

METHODS AND APPARATUSES TO INCREASE INTRAOCULAR LENSES POSITIONAL STABILITY

CROSS REFERENCES TO RELATED APPLICATIONS

This application claims the benefit under 35 U.S.C. § 119(e) of U.S. Provisional Patent Application No. 62/556,853, filed Sep. 11, 2017, which is incorporated herein by reference in its entirety.

BACKGROUND OF THE INVENTION

Field of the Invention

This application is directed to methods and apparatuses to improve positional stability in intraocular lens systems when implanted in the capsular bag.

Description of the Related Art

Cataract is a common cause for vision loss in aging individuals. Cataract is a progressive condition in which the natural lens within the eye becomes opaque. This process can eventually lead to blurred, obscured vision and even blindness as the condition progresses further. The good news for many patients is that a well-known procedure can restore vision to a great extent. The procedure involves removing the natural lens containing the cataract and thereafter replacing the focusing function of the natural lens with a prosthetic lens, commonly referred to as an intraocular lens or an "IOL". The membrane containing the natural lens, called the "capsular bag", is not affected by the cataracts and is left intact, except for an opening in the anterior side needed to accommodate removal of the natural lens and insertion of the IOL.

IOLs are usually formed by a single piece that contains the optical part (which provides the focusing function mentioned above) and a device to fixate the IOL in the capsular bag. For example, the TECNIS® family of IOLs has a 13 mm dimension in a larger axis (between ends of the haptics) and the optical part has a 6 mm diameter optical zone. IOLs can be formed by more pieces (e.g., two lenses) and/or more complex platforms (e.g., to provide for displacement of lenses with respect to each other). The device is fixated in the capsular bag by applying force in the inner part of the capsular bag.

Typically the lenses are inserted into the eye in an injector apparatus that is similar to a syringe but with a larger bore and usually with some structure for folding the IOL. More complex, larger IOLs tend to call for larger bore injectors which is counter to most patient and surgeon preference.

SUMMARY OF THE INVENTION

There is a need for a new technology for improving positional stability of IOLs. Rotation in toric IOLs, axial position, tilt and decentration are major causes of residual refractive errors after surgery. Moreover, embodiments disclosed herein enable larger size IOLs which deliver more functionality to be placed in the eye without excessive trauma or other complications. In various embodiments, IOLs can be configured to be assembled within the eye to provide advantageous implantation and performance.

In one embodiment, a multi-piece IOL assembly is provided that includes a platform and an optic. The platform has an outer periphery configured to couple with an inner periphery of an eye (e.g., an inner periphery of a capsular bag, or a periphery of the anterior chamber or the posterior chamber of the eye). The platform has an inner periphery surrounding an inner zone of the platform. The optic has an optical zone, an outer periphery and a retention mechanism disposed on the outer periphery. The optic is configured to be disposed in the inner zone of the platform and to extend to a location between the inner periphery and the outer periphery of the platform to be secured to the platform at the location.

In another embodiment, a method of implanting an IOL in an eye is provided. In the method, an interior space, e.g., an anterior chamber or a posterior chamber, of an eye is accessed. A platform is advanced into the interior space, e.g., into the anterior or posterior chamber. The platform has an outer periphery and an inner periphery surrounding an inner zone of the platform. The platform is coupled with an inner periphery of the eye. An optic is advanced into the interior space, e.g., into the anterior or posterior chamber of the eye after the platform is advanced into the interior space, e.g., into the anterior or posterior chamber. The optic has an optical zone and an outer periphery. The optical zone of the optic is advanced into the inner zone of the platform. The outer periphery of the optic is advanced to a location of the platform between the outer periphery and the inner periphery thereof.

In another embodiment, a platform to place the IOL is created or formed in the capsular bag by femtosecond laser or other segmenting or emulsifying device. During the cataract surgery, an inner part of the crystalline lens disposed about the optical axis of the eye is removed leaving a platform structure in the outer part of the crystalline lens. The outer part can be configured with an inner periphery that is configured for placing and for securing the IOL inside the capsular bag.

In one example, a method of improving a patient's vision is provided. A platform is provided for supporting an optic in an eye of a patient. The platform has a one or a plurality of notches. An optic is coupled with the platform such that an optical zone thereof is central portion of the platform. A retention mechanism of the optic is disposed in the notch or in one of the notches of the plurality of notches in an initial position. Following placement of the optic, an observation is made as to whether a more anterior or more posterior position could provide better optical performance. The platform is modified to allow the optic to move from the initial position to an adjusted position to provide better optical performance.

In the foregoing methods, one or more notches can be formed or eliminated to allow the optic to move from the initial position to the adjusted position.

In another method, cutting energy is directed into an eye to remove a central portion of a natural lens capsule from the eye. Cutting energy is directed into the eye to form an inner periphery in a portion of the lens capsule that is to remain after the central portion thereof has been removed. The inner periphery has one or more notches configured to receive retention structures of an optic to be coupled with the inner periphery of the remaining portion.

In one embodiment, the IOL is fixed in to the capsular bag by photobonding. The photobonding is applied to the outer part of the platform to the inner part of the capsular bag to prevent IOL rotation and displacement.

In another embodiment, the piggyback IOL is fixed in an existing IOL implanted in the capsular bag by photobonding.

BRIEF DESCRIPTION OF THE DRAWINGS

The systems, methods and devices may be better understood from the following detailed description when read in conjunction with the accompanying schematic drawings, which are for illustrative purposes only. The drawings include the following figures:

FIG. 5A is a cross-sectional view of one embodiment of the platform of FIG. 2 showing a single-piece IOL disposed therein;

DETAILED DESCRIPTION OF THE PREFERRED EMBODIMENT

This application is directed to apparatuses, systems and methods that enable a broader range of IOL design freedom. Broader design freedom is provided at least in part by enabling a more voluminous IOL to be implanted without requiring a much larger incision size. IOL designs have heretofore been limited by a maximum size of a corneal incision that is used to deliver the IOL into the eye, specifically into the capsular bag of the eye. Smaller incisions of a diameter of about 2.75 mm to 3.2 mm are preferred by surgeons in order to reduce the risk of complications during surgery. Examples of complications that can arise from larger incisions are surgically induced astigmatism and post-operative trauma. This small size constrains the possibilities of new IOL designs for example in terms of the optical zone diameter and the central thickness of the optical part of the IOL.

Additionally, this application also addresses methods to increase positional stability inside the capsular bag. Although different platforms are available in the market, rotation in toric IOLs, displacement in the axial position, tilt and decentration, are still major causes of post-operative refractive errors (defocus, astigmatism and higher order aberrations). The methods can be also applied to piggyback IOLs designs that can be used to correct existing post-operative refractive errors from a previous cataract surgery, or to provide new features to an implanted IOL design in pseudophakic patient (e.g. a multifocal design in a patient previously implanted with a monofocal IOL).

I. Single-Piece IOL Placement in an Eye

Figure 1:
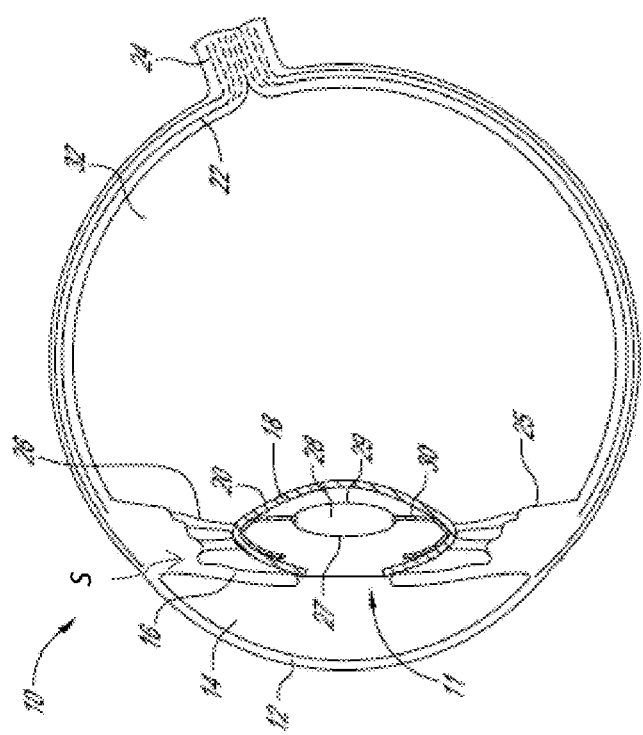
FIG. 1 is a cephalad-caudal cross-section of the eye taken in the anterior-posterior direction, showing a single-piece IOL placed therein.

FIG. 1 shows one approach to treating an eye 10 with a cataract. A cornea 12 encloses an anterior chamber 14 of the eye 10. Light entering the cornea 12 passes through the anterior chamber 14 also passes through an iris 16. The iris 16 is a muscle that constricts and expands to regulate the amount of light passing into the natural lens, which is located between the anterior chamber 14 and the vitreous 32. In an unaltered eye not impaired with cataract the cornea and the natural lens together focus light at the back of the eye. FIG. 1 shows that the natural lens has been removed leaving the capsular bag 18 intact. The capsular bag 18 is supported by zonules 26 which are coupled to the periphery of the bag 18 on one end and to the ciliary body 25 on the other end. The ciliary body 25 can act on the bag 18 directly through the zonules 26. Light entering the eye 10 passes through the cornea 12, an anterior surface 27, a central zone of a lens body 28, and a posterior surface 29 of an IOL 11. An image can be focused by the cornea 12 and the IOL 11 on the retina 22 located at the back of the eye. The focused image is detected by the retina 22 and the information detected is conveyed to the brain by the optic nerve 24. Haptics 30 support the periphery of the lens body 28 at the interior surface of the capsular bag 18.

II. Multi-Piece IOL Capable of Sequential Insertion & Intraocular Assembly

Figure 2:
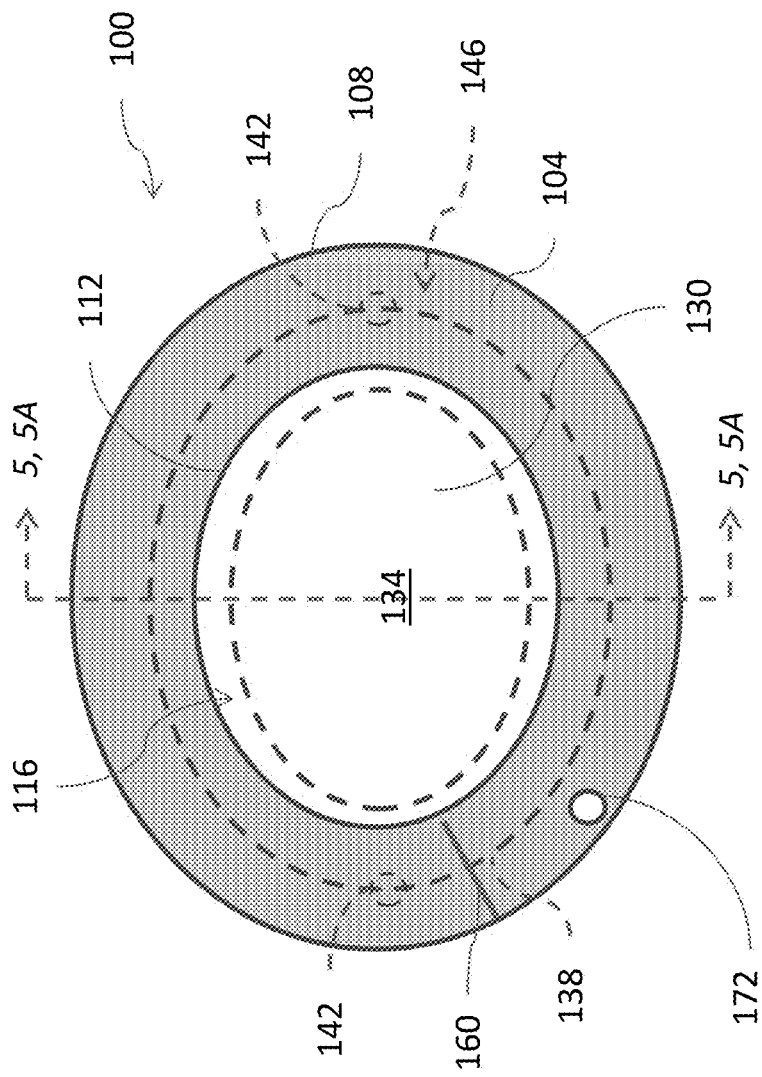
FIG. 2 is an anterior side view of a multi-piece IOL assembly.

FIG. 2 shows a multi-piece IOL assembly 100 that can be implanted in the eye in separate pieces and assembled therein. The multi-piece IOL assembly 100 includes a platform 104 and an optic 130. The optic 130 provides refractive power to replace a natural or a previously placed lens and/or to supplement either a natural or a previously placed lens.

The platform 104 includes an outer periphery 108 and an inner periphery 112. The outer periphery 108 surrounds the inner periphery 112 and also surrounds an inner zone 116. The outer periphery 108 can be circular with a diameter of 10 mm. In one embodiment, the inner periphery 112 also is circular and has a diameter of between about 4 mm and about 9 mm, in some cases between 5 mm and 8 mm, and in one specific example about 6.5 mm. The inner zone 116 can be a through hole in a central zone of the platform 104. The inner zone 116 can be surrounded by the inner periphery 112 of the platform 104. The outer periphery 108 can be configured to couple with an inner periphery of an eye. For example, the outer periphery 108 can be configured to couple with the inside surface of the capsular bag 18 or with a sulcus S of the eye.

The platform 104 is configured to be assembled with the optic 130 in the eye in certain techniques. The platform 104 can have a location 146 configured for securing the optic 130. The location 146 can be an annular zone of the platform 104 between the outer periphery 108 and the inner periphery 112. The location 146 can comprise one or more grooves or slots that can hold one or more optics. The location 146 can include a mechanical interface such as a projection or protrusion as discussed further below.

The platform 104 and the optic 130 can comprise materials that have different light transmission characteristics. For example, the platform 104 can have zero transmittance in at least the visible wavelengths of light to block transmission of at least visible wavelengths of incident. As another example, the platform 104 can comprise materials that transmit less than or equal to about 10% of the incident light. In some embodiments, the platform 104 can be configured to transmit less than 1% of light in the visible wavelength range, less than 2% of light in the visible wavelength range, less than 3% of light in the visible wavelength range, less than 5% of light in the visible wavelength range.

The optic 130 can comprise materials that transmit substantially all the incident light in the visible wavelength range. For example, the optic 130 can comprise materials that transmit greater than or equal to 80% of the incident light in the visible wavelength range, greater than or equal to 85% of the incident light in the visible wavelength range, greater than or equal to 90% of the incident light in the visible wavelength range, greater than or equal to 95% of the incident light in the visible wavelength range, or greater than or equal to 99% of the incident light in the visible wavelength range.

The optic 130 can be configured to have visible light transmittance in a central vision zone and reduced visible light transmittance towards the periphery of the optic 130. In some embodiments, the visible light transmittance can decrease in a determined manner from the center of the optic 130 to the periphery of the optic 130. The optic 130 can comprise materials that have UV filtering characteristics. For example, the optic 130 can be configured to block incident UV light. As another example, the optic 130 can be configured to transmit less than or equal to 5% (e.g., less than or equal to 3%, less than or equal to 2%, or less than or equal to 1%) of the incident UV.

Figure 5:
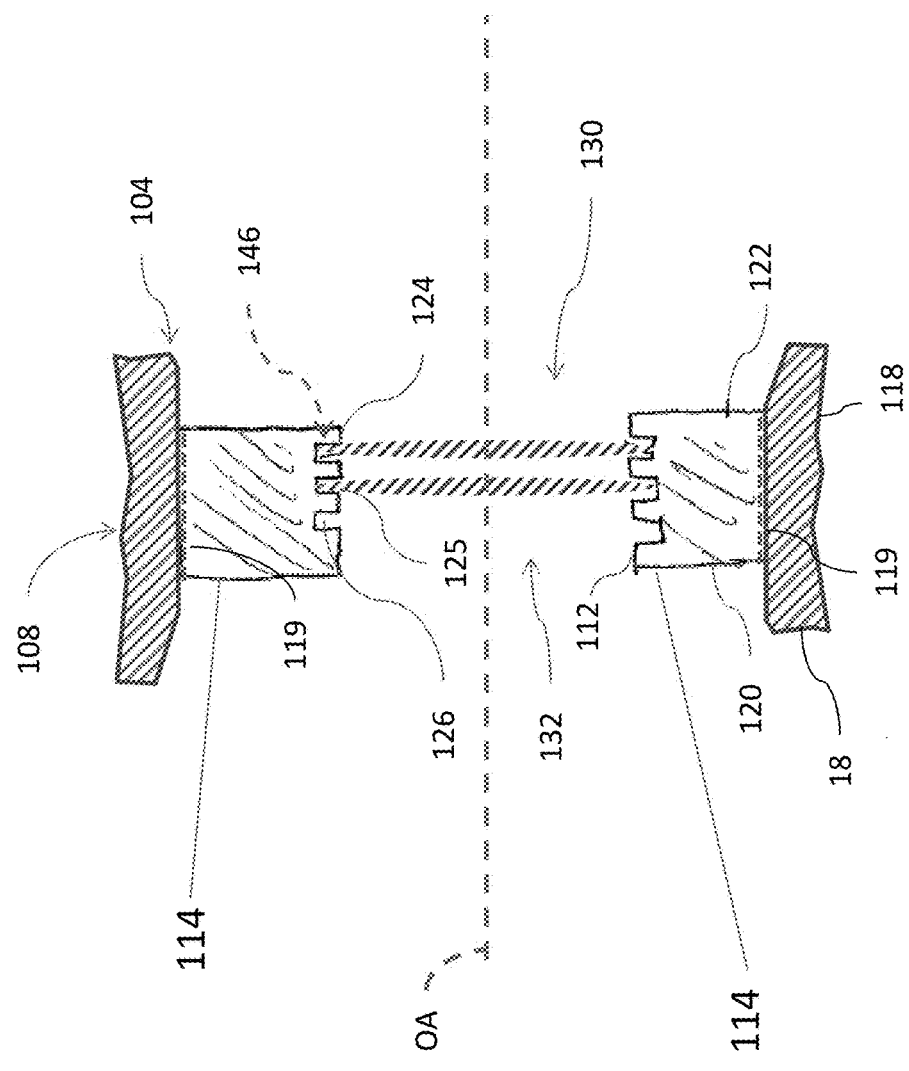
FIG. 5 is a cross-sectional view of one embodiment of the platform of FIG. 2 showing an optic disposed therein.

FIG. 5 shows that the platform 104 can include an annular member 114. The annular member 114 can be defined or disposed between the inner periphery 112 and the outer periphery 108. The annular member 114 can comprise an outer surface 118, an anterior surface 120, and a posterior surface 122. The outer surface 118 can be a continuous surface, e.g., a surface that extends 360 degrees around the inner zone 116. The outer surface 118 can be configured to provide 360 degree contact between the platform 104 and the anatomy, e.g., with an interior periphery of the eye such as with the inside of the capsular bag 18 or with the sulcus. By providing continuous contact about the outer periphery 108, e.g., along the outer surface 118, the platform 104 can be coupled to the anatomy in a manner that reduces, minimizes or eliminates cell migration along the outer surface 118 between the platform 104 and the anatomy, from the anterior surface 120 to the posterior surface 122 of the platform 104, or generally around the multi-piece IOL assembly 100. The outer surface 118 can have a 360 degree square edge design or a 360 degree sharp edge design that provides a 360 degree contact between the platform 104 and the anatomy to reduce, minimize or eliminate migration of epithelial cells.

In certain embodiments, the platform 104 includes at least one slot 124 disposed therein. The slot 124 can be enclosed at a radially outward position by a recessed portion of the inner periphery 112. The recessed portion can be enclosed by the outer surface 118. FIG. 5 shows that in one embodiment of the platform 104 includes a second slot 125. In one embodiment the platform 104 includes a third slot 126. The slot 124 and the additional slots 125, 126 can be aligned in an anterior-posterior direction in one embodiment. In various methods discussed below the slots 124, 125, 126 can be used individually or together to support the optic 130 and/or a second optic 132 and in some cases a third optic. Although three slots and two optics are shown any combination of slots can be provided and the number of optics can be pre-defined or can be surgeon determined based upon factors such as intraoperative aphakic, or pseudophakic measurement. The slot 124 can be enclosed on anterior and posterior sides by recessed portions of the inner periphery 112 and/or by the anterior surface 120 and the posterior surface 122.

Figure 3:
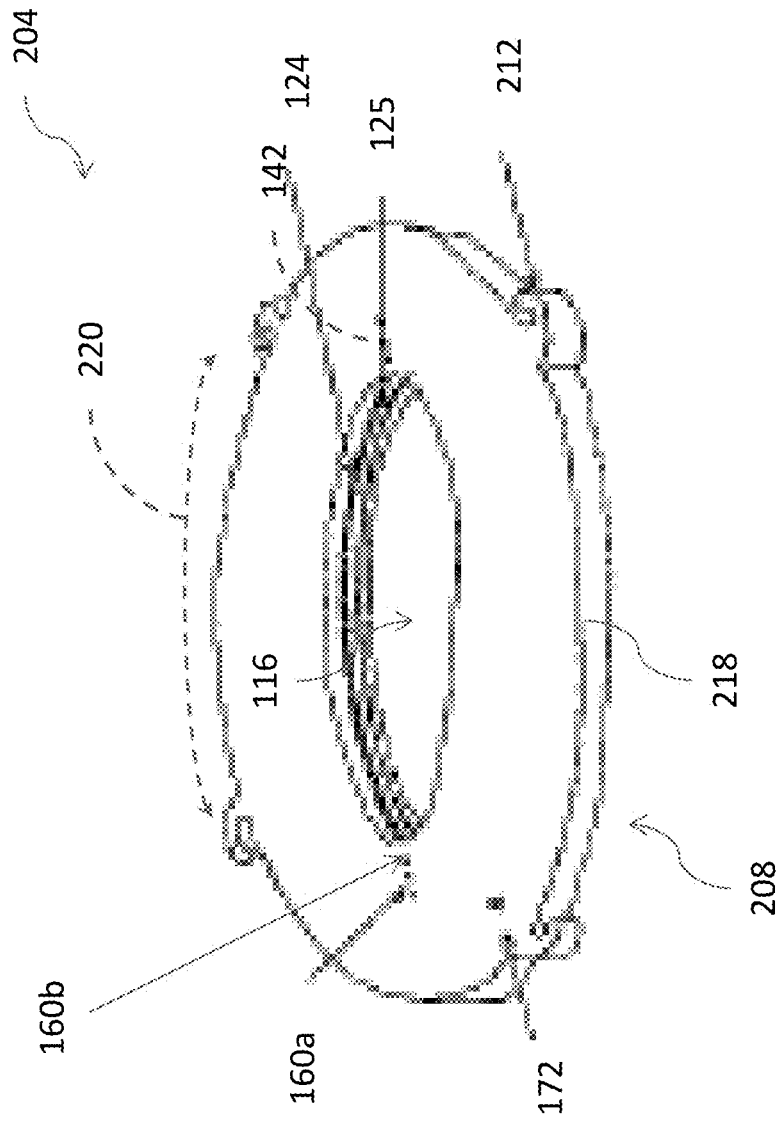
FIG. 3 is a perspective view of a platform that can be inserted separately into the eye and that can be assembled with one or more powered optics to provide a desired level of optical power.

Referring to FIGS. 2 and 3, the platform 104 can include various indicia to assist in placement of the platform 104 in the eye. For example, the platform 104 can include indicia 160 for aligning the platform 104 with the eye. The indicia 160 can be configured as anatomical indicia to align with particular ocular anatomy, for example to align to a particular zone of the anterior segment of the eye. The indicia 160 can comprise optic indicia to align the optic 130 within the eye. For example, certain vision disorders arise from rotational variation in the eye system. Astigmatism is an example. For such conditions improved outcomes arise from aligning the optic 130 configured with different powers at different angular positions at the specific angular position requiring such powers.

An aperture 172 can be provided as one example of a structure for rotationally positioning the platform 104. If the indicia 160 are configured as anatomical indicia, it may be desirable to rotate the platform 104 after it has been placed in the eye against the interior periphery to which it is to be coupled. A slender surgical instrument such as a curette can be inserted into the aperture 172 to engage the platform 104 so that the platform 104 can be rotated within the eye. Once positioned, the instrument can disengage the aperture 172 leaving the platform 104 in place. The amount of rotation by engagement with the aperture 172 can be guided by the indicia 160 if configured as anatomical indicia.

It may be possible to use the indicia 160 for both rotationally positioning the platform 104 to the ocular anatomy and for positioning the optic 130. In some embodiments two separate indicia are provided. A first indicia 160a is provided for aligning with the anatomy and a second indicia 160b is provided for aligning the optic 130 to the platform 104 as depicted in FIG. 3. The first and second indicia 160a and 160b can be spaced apart from each other on a surface of the platform 104.

In some embodiments the indicia 160 is/are disposed on the anterior surface (e.g., surface 120 of FIGS. 5 and 5A) of the platform 104 to enhance the visibility of the indicia 160. In some cases, the platform 104 is clear and the indicia 160 can be positioned on the posterior surface (e.g., surface 122 of FIGS. 5 and 5A) of the platform 104.

FIGS. 2, 5 and 5A illustrate embodiments that are configured to be joined along a surface area rather than at discrete spaced apart locations using mechanical anchors. FIG. 5 shows that the outer surface 118 can be placed in directed contact with an inside surface of the capsular bag and the outer surface 118 can thereafter be joined along an interface 119 to the inside surface of the capsular bag 18 by any suitable bonding or securing technique. For example, bonding can be achieved by laser fusion, by chemical gluing, photocuring, or by photobonding the platform 104 in or to the capsular bag 18 along the interface 119.

Photocuring is a technique in which the components to be secured are brought into contact and exposed to UV radiation or visible radiation. The polymer properties of one or both components to be secured can be altered as a result of exposure to UV radiation. For example, one or both components can harden and/or cross-linking of the molecules of the material of one or both components can occur which can facilitate bonding.

An example of ophthalmic applications of photocuring is treatment for keratoconus in which Vitamin B is applied to the cornea, where after it is exposed to UV light causing corneal crosslinking and/or strengthening the cornea.

Some implementations of the platform 104 can comprise materials that can harden and/or exhibit cross linking when exposed to UV radiation and adhere to the capsular bag 18. In some embodiments, a chemical that can harden and/or exhibit cross linking when exposed to UV radiation can be disposed between the platform 104 and the capsular bag 18. The chemical can facilitate bonding between the platform 104 and the capsular bag 18 when exposed to UV radiation. Various materials that can be photocured are described in U.S. Pat. No. 7,276,544 which is incorporated herein by reference in its entirety.

Laser fusion is a technique in which different layers of material are bonded by optical energy. One or more outer layers of material on which the laser light is incident can be configured to transmit the incident laser light and one or more inner layers of material are configured to absorb the light transmitted by the one or more outer layers. The one or more inner layers of material can melt as a result of the absorbed optical energy and fuse with the one or more outer layers. In this manner the different layers or materials are welded or joined together.

Lasers that emit radiation in the far ultraviolet spectral region, such as, for example, an excimer laser or lasers that emit radiation in the far infrared spectral region, such as, for example, a $CO_2$ laser can be used for laser fusion.

If chemical agent (e.g., a dye) is applied to or released from one or both the components that are being fused (e.g., the platform) to facilitate or enhance bonding, then lasers that emit radiation in wavelength ranges which activate the chemical agent can be used.

Other lasers that can be used for laser fusion include an argon ion laser, Nd:YAG laser and/or $KTiOPO_4$ (potassium titanyl phosphate) laser.

Example photobonding techniques that can be used to join the platform 104 along the interface 119 are discussed in WO2016/142490A1, the entire contents of which are hereby incorporated by reference herein. In some embodiments, the platform 104 can be joined to the inside surface of the capsular bag 18 by a surface adherent that can self-adhere to the inside surface of the capsular bag 18. US2011/0029074 provides examples of surface adherents that can be provided on the outer surface 118 of the platform 104. For example, gecko feet microfibers as described in US Publication No. 2011/0029074 which is incorporated herein in its entirety can be used as a surface adherent. These surface adherents preferably provide enhanced positional stability and can be configured to be permanent due to the ability to change the optical properties of the optic 130 and/or add a second lens as a piggyback lens. Although the foregoing discussion has been focused on bonding or securing to the inside surface of the capsular bag 18, these techniques can also be applied to the sulcus S or another stable inner periphery of the inside of the eye 10.

FIG. 3 shows an embodiment of a platform 204 that is similar to the platform 104 except as described differently below. The platform 204 can provide all the same functions discussed above in connection with the platform 104. The platform 204 can also be configured to provide discrete, spaced apart point contact with the inside surface of the eye 10. For example, one or more haptics 212 can be at the provided along the outer periphery 208 of the platform 204. The haptics 212 can comprise anchors that extend from an outer surface 218 of the platform 204. The haptics 212 can have any haptic configuration. In certain embodiments, the haptics 212 comprise short hook-like features that extend only a short distance from the outer surface 218. The outer surface 218 may in fact be in contact with the ocular anatomy to which the haptics 212 engage in the locations of the platform 204 between the spaced apart haptics 212. A contact zone 220 can be along an arcuate portion of the outer surface 218 between two adjacent haptics 212. The arcuate zone 220 can provide for direct contact between the haptics 212 between the two adjacent haptics 212. In the illustrated embodiment, the haptics 212 are spaced apart by equal distances, e.g., each spaced from two adjacent haptics 212 by an approximate arc of 90 degrees. There can be more or fewer than four haptics. For example, there can be two, three, five, six, seven or eight haptics in various embodiments. Also, the haptics 212 can be located other than at equal spacing from one another. As discussed above, the platform 204 can be disposed to contact the inner periphery of the capsular bag and attached to the inner periphery of the capsular bag by bonding such as, for example, by laser fusion, by chemical gluing, photocuring, or by photobonding. When attaching the platform 204 to the inner periphery of the capsular bag, the haptics 212 can be bonded directly to the inner periphery of the capsular bag by bonding such as, for example, by laser fusion, by chemical gluing, photocuring, or by photobonding.

Figure 4:
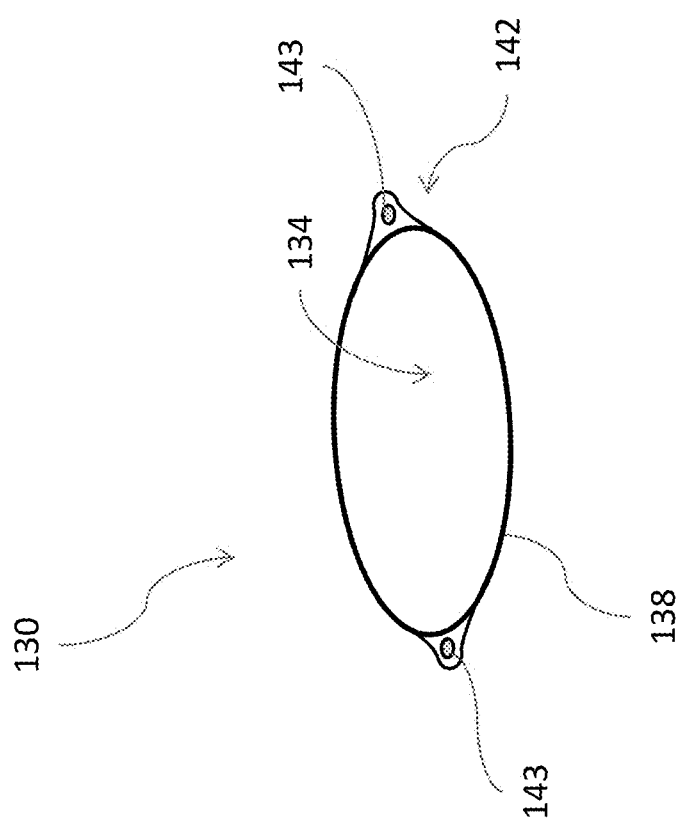
FIG. 4 is a perspective view of an example of an optic that can be inserted separately from the platform of FIG. 3 but thereafter assembled therewith in the eye.

FIG. 4 shows the optic 130 in further detail. The optic 130 includes an optical zone 134. The optical zone 134 is surrounded by an outer periphery 138 of the optic 130. The optical zone 134 is configured to combine with the cornea 12 to provide overall optical power of the eye 10. The optical zone 134 can provide refractive power to replace a nature lens as in the case of a cataract procedure. The optical zone 134 can provide additional ocular benefits, for example including a filter of at least one spectrum of light. The optical zone 134 can provide an ultraviolet (UV) filter for example. The optical zone 134 of an optic can be configured, design, produced or selected to benefit an adjustment procedure. One type of adjustment procedure involves observing during an initial cataract procedure that the power provided by the optic 130 is not as expected. A second optic 132 as depicted in FIG. 5 can be placed in the platform 104 anterior of the first optic 130. The second optic 132 can have an optical zone 134 that is configured to provide the additional power needed by the eye having the first optic 130 or to reduce the power of the eye having the first optic 130. The second optic 132 can have an optical zone 134 that is configured to correct optical aberrations, e.g., glistening or intolerable halos from a multifocal or other advanced optical design.

The first optic 130 or the second optic 132 (or additional optics) can provide therapy other than restoring proper refraction. In one embodiment, the first optic 130 and the second optic 132 are configured along with the platform 104 to provide varying power. One or both of the first optic 130 and the second optic 132 are configured to move transverse to, e.g., perpendicular to, the optical axis OA. Such movement can cause highest power regions of the optical zone 134 of the first and second optics 130, 132 to overlap more (yielding increased power) or to overlap less (yielding decreased optical power). The transverse movement can be provided during the surgery prior to fully engaging the first and second optics 130, 132 to the platform 104 or can be facilitated by configuring the platform 104 to be sufficiently flexible to be moved or deformed by the zonules 26 and/or the ciliary body 25 to provide accommodation. Further details of such power change are discussed in U.S. Pat. No. 3,305,294, which is incorporated by reference herein in its entirety.

In a two optic embodiment, the optic 130 can include a 6.5 mm diameter. The optic 130 can be configured to optically compensate for corneal aberrations. For example, the optic 130 can include an aspheric anterior surface to compensate for corneal spherical aberrations. The power of the optic 130 can be around +10 diopter (D), around +20 D, around +30 D, as examples. The optic 130 can have a spherical posterior surface in some examples. The second optic 132 can include a 6.5 mm diameter. The second optic 132 can have an aspheric anterior surface to provide zero spherical aberration in one embodiment. The second optic 132 can have powers in the range of −5 D to +5 D. The second optic 132 can have a spherical posterior surface. In a kit, a plurality of optics 130 can be provided, e.g., +10 D, +20 D, +30 D, a plurality of second optic 132 can be provided, e.g., −5 D to +5 D in 0.5 D increments, and the platform 104 can be provided.

The optic 130 can also incorporate optics that deflect the focal point of the eye away from the natural focal area, which is referred to as the fovea. In some conditions such as macular degeneration, retinal cells at the fovea do not function properly. Most eyes benefit from additional locations on the retina, sometimes referred to as peripheral retinal locations because these locations are spaced away from the fovea, where a focused image can be detected and interpreted by the brain. Thus, there is an opportunity to configure the optic 130 with the optical zone 134 being able to deflect light away from the fovea to one of these peripheral locations. The optical zone 134 thus can be configured to address macular degeneration and other diseases that reduce or eliminate the ability to detect an image focused at the fovea. Examples of such lenses are discussed in U.S. Publication No. 2015/0250583 which is incorporated herein by reference in its entirety.

Even for patients without any foveal function concern, the optic 130, the second optic 132, or both the optic 130 and the second optic 132 can be configured to provide enhanced image quality for a larger field of view by reducing, e.g., by minimizing or eliminating, peripheral aberrations. Examples of such lens are discussed in U.S. Publication No. 2015/0320547 which is incorporated herein by reference in its entirety.

The optic 130 or the second optic 132 can incorporate any optical design, such as multifocal, extended range of vision, toric, and other designs. Toric lenses are susceptible to rotation after implantation. Since, the astigmatic correction provided by the toric lens can vary with rotational alignment of the toric lens, rotational stability of toric lenses is advantageous. The platform 104 and/or 204 can advantageously increase the rotational stability of toric lenses.

FIG. 4 shows that the optic 130 (or the second optic 132) can include a retention mechanism 142 disposed along the outer periphery 138. In one embodiment, the outer periphery 138 includes two retention mechanism 142 disposed at opposite, e.g., at diametrically opposed sides, of the outer periphery 138. The retention mechanism 142 can include one or more projections 143 oriented in an anterior-posterior direction (e.g., parallel to the optical axis of the optical zone 134). The projections 143 can be similar to detent features, comprising hemispherical projections. The platform 104 preferably includes mating recesses the can receive the projections 143 of the retention mechanism 142. The platform 104 can have an array of recesses along an arc at the location 146 where the optic 130 engages the platform 104. This array allows the optic 130 to be rotated from one retention site of the platform 104 to another retention site. This allows a rotationally asymmetric optic 130 to be adjusted until the proper alignment results. Also, the array of recesses can be provided in one or in each of the slots 124, 125, 126. These are examples of mechanisms that can be used to provide for displacement and fixation of the optic to control lens positioning within an eye to reduce one or more of tilt aberration, decentration aberration and pseudophakic power estimation error. In some implementations, the optic 130 can be configured to be compressible and have a size that is somewhat larger than the size of the inner periphery 112. The optic 130 can be compressed prior to being inserted into the location 146 of the holder 104. The optic 130 can expand after insertion into the location 146 and held in place be compressive forces applied by the holder 104.

The projection 143 and recess configuration of the retention mechanism 142 and the platform 104 can provide a tactile feedback benefit to the surgeon. For example, if the surgeon moves the optic 130 about the optical axis OA within the platform 104 from a first rotational position to a second rotational position, the surgeon will be able to feel the retention mechanism 142 engaging the recess in the slot 124, the slot 125, or the slot 126 of the platform 104. The engagement of the retention mechanism 142 can assure that a rotationally asymmetric optical zone 134 (e.g., as in a toric lens) will continue to remain at the proper orientation. This is because the platform 104 can be securely affixed to an inner periphery of the eye 10 using any of the techniques discussed herein. The engagement between the retention mechanism 142 with the platform 104, e.g., projections 143 of the retention mechanism 142 with recesses in the platform 104 can assure that the rotational position of the optic 130 (or the second optic 132 or other optics in the platform 104) is maintained.

The platform 104 and the optic 130 can be configured to reduce, minimize or eliminate aberrations around the inner periphery 112. For example, as discussed above, the platform 104 and the optic 130 can have different transmittance characteristics. The platform 104 can be at least partially opaque. The platform 104 can be configured to prevent transmission of substantially all incident light. The platform 104 can be tinted sufficiently to prevent light from propagating out of the optic, e.g., through internal reflection toward the retina or out of the eye through the platform 104. Some embodiments provide a variation, e.g., a gradual change, in transmittance between the optical axis OA and the inner periphery 112 of the platform 104. This allows the platform 104 to block reflected light that could create aberrations due to the optical behavior of the platform 104 but prevent the presence of a drastic difference in opacity between the platform 104 and the optic 130 from creating other aberrations.

Figure 6A:
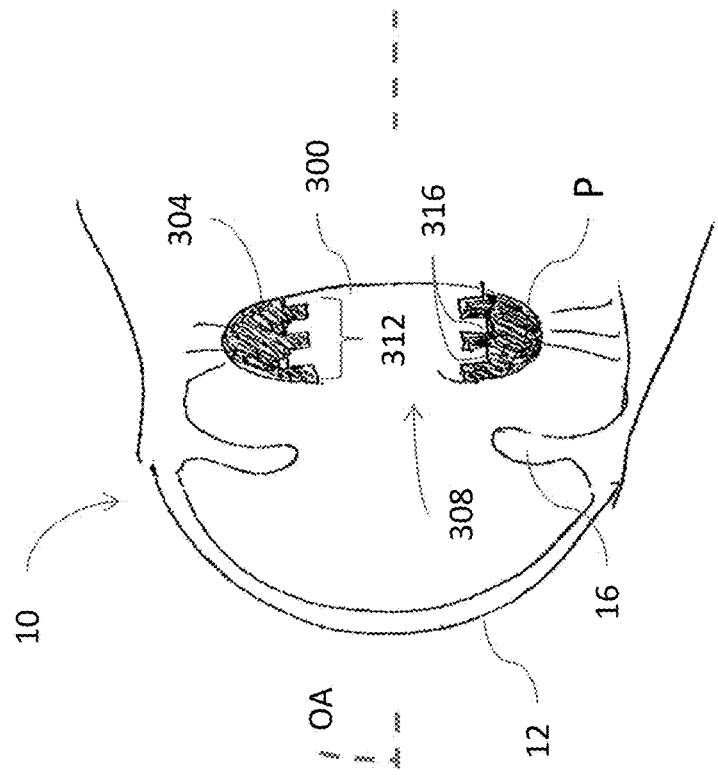
FIGS. 6A and 6B illustrate one embodiment of a method showing cross-sectional view of a natural crystalline lens before and after ablation to create a platform in an inner periphery of an outer part of the crystalline lens.
Figure 6B:
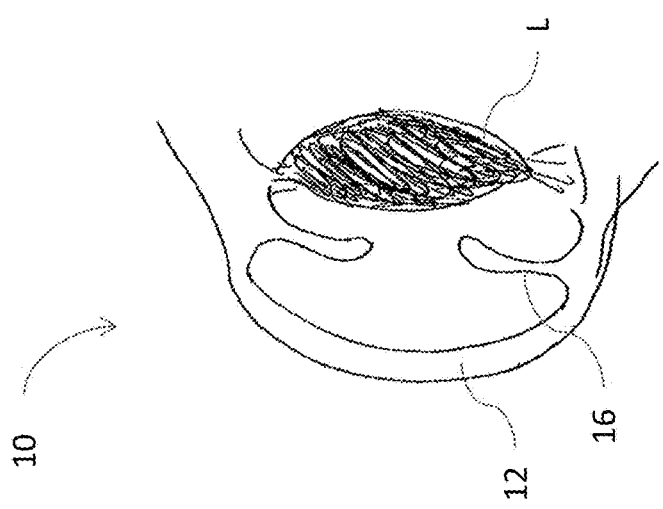

III. Formation of a Natural Platform for IOL Implantation in the Crystalline Lens FIGS. 6A and 6B shows other approaches to improving positional stability in an intraocular lens system by forming a platform P in a natural eye structure. The platform P can have discrete positions for placement of IOLs.

FIG. 6A shows a natural eye 10. The cornea 12 of the eye 10 is intact as is the natural lens L. The iris 16 is shown in a relatively constricted state. As discussed above, a variety of technologies can be used to remove parts of the natural lens L. In a conventional procedure the capsular bag 18 is formed by removing substantially all of the interior volume of the lens L. This normally results in a thin membrane as shown in FIG. 1. The thin membrane has a continuously concave inner surface if the membrane is propped open. A central portion of the lens is removed such that an open zone 308 can be formed in the lens. In some cases, the open zone 308 can be enclosed by a thin wall 300 at a posterior portion thereof. Also, a peripheral portion 304 of the lens can be left intact. The size location and shape of the open zone 308 can be formed by directing a femtosecond laser or a light source directing ultraviolet picosecond pulses through the cornea at precisely planned depths.

The peripheral portion 304 can define an inner periphery 312 of the platform P in the eye. The inner periphery 312 can include a profile not found in the ocular anatomy. The inner periphery 312 can include one or a plurality of notches 316. The notches 316 can be separated along the optical axis OA. In one embodiment, the notches 316 are spaced from each other by a separation distance or spacing that provide a noticeable change in focal point at the retina. Such spacing can be sufficient to provide the equivalent of a change in power, e.g., +/−0.25 diopters, +/−0.5 diopters, +/−0.75 diopters or any other increment but generally less than 1 diopter between adjacent notches.

By preparing the lens L in the foregoing manner with notches 316 built into the peripheral portion 304 greater stability and selectability can be provided for implanting lenses. The peripheral portion 304 can be much thicker in the equatorial plane (e.g., the plane transverse to the optical axis OA that intersects the widest part of the lens L. This greater thickness enables the platform P formed in the eye 10 to retain much more rigidity than a conventional capsular bag 18 formed in an eye using standard techniques such as phacoemulsification or even using a femtosecond laser. The notches 316 can be configured to engage peripheral portions of optics as discussed further below. So in addition to being more rigid than a conventional capsular bag, the platform P can engage optics in a way that provides for their rotational stability.

Figure 7:
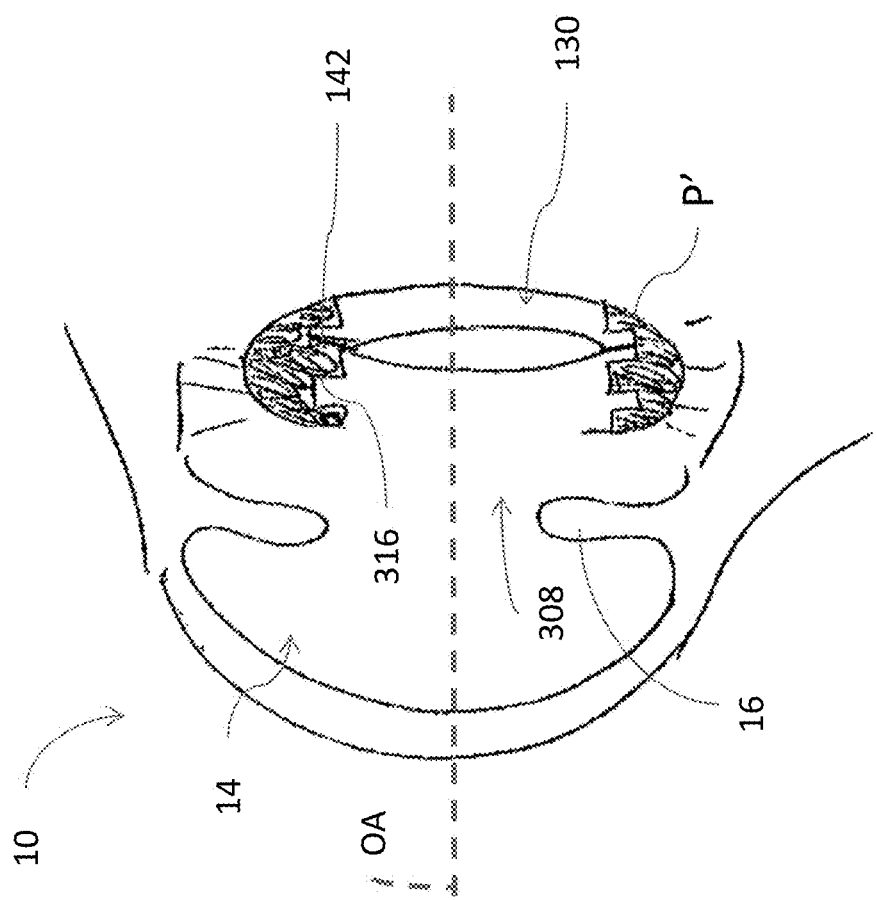
FIG. 7 is a cross-sectional view illustrating one embodiment of a method of using the platform created in the natural crystalline lens of FIG. 6 showing a single-piece IOL disposed therein.

FIG. 7 shows a modified technique in which a platform P' is formed in a lens capsule. The platform P' is similar to the platform P except that rather than having three notches 316 the platform P' has two notches 316. In certain embodiments where fewer notches are provided a greater spacing may be provided between adjacent notches. A greater spacing can have an effect of increasing a difference in optical performance for a same lens placed in the different notches 316.

FIG. 7 illustrates a part of a method placing the optic 130 in the platform P'. The optic 130 can be placed into the eye by making a small incision peripheral to an optical zone of the cornea 12. The iris 16 can be dilated to move it out of the way during the procedure. Thereafter, an injector can be inserted through the incision into the anterior chamber 14 of the eye 10. The optic 130 can be advanced into the eye through the injector. Thereafter, the optic 130 expand to the shape seen in FIG. 7. The retention mechanism 142 can be coupled with any one of the notches 316. FIG. 7 shows that the optic 130 can be advanced posteriorly in the eye 10 until the retention mechanism 142 is aligned with the posteriormost notch 316. Thereafter the retention mechanism 142 can be advanced into the notches 316. The retention mechanism 142 can provide for mechanical engagement in the notch 316. Other techniques can secure the optic 130 in the notch 316 as discussed below.

IV. Bonding of the IOL in the Capsular Bag or Other Natural Lens Structure

As discussed elsewhere herein, photobonding and related procedures can be used to secure an implanted structure in the eye 10. For example, FIG. 5 shows the outer periphery 108 of the platform 104 bonded to the capsular bag 18 along the interface 119. Photobonding and other similar methods could be used to secure an optic or an IOL directly to what remains of a lens capsule after central portions thereof have been removed (e.g., into a capsular bag, into a platform P formed in a remaining portion of a natural lens capsule, as discussed above).

FIG. 1 shows an IOL placed in a capsular bag 18 formed in a conventional manner. Photobonding can provide for a bonding interface between peripheral haptics and the inside periphery or surface of the eye 10. Such techniques can also be use greatly enhance stability of conventional IOLs in the capsular bag 18. This can provide an advantage for IOLs that have rotationally asymmetric optics, such as toric IOLs.

FIG. 7 shows the optic 130 placed in the platform P'. The optic 130 can be secured in the platform P', e.g., in one of the plurality of notches 316 using photobonding. A bonding interface can be formed between a periphery of the optic 130 and the concave space in the notches 316. The retention mechanism 142 can be configured to enhance bonding, e.g., by being formed of a material or by having the material disposed thereon, which material is suitable for photocuring, laser fusion or photobonding. Further details of photocuring, laser fusion or photobonding are set forth elsewhere herein and the description thereof is incorporated to supplement this discussion.

Figure 8:
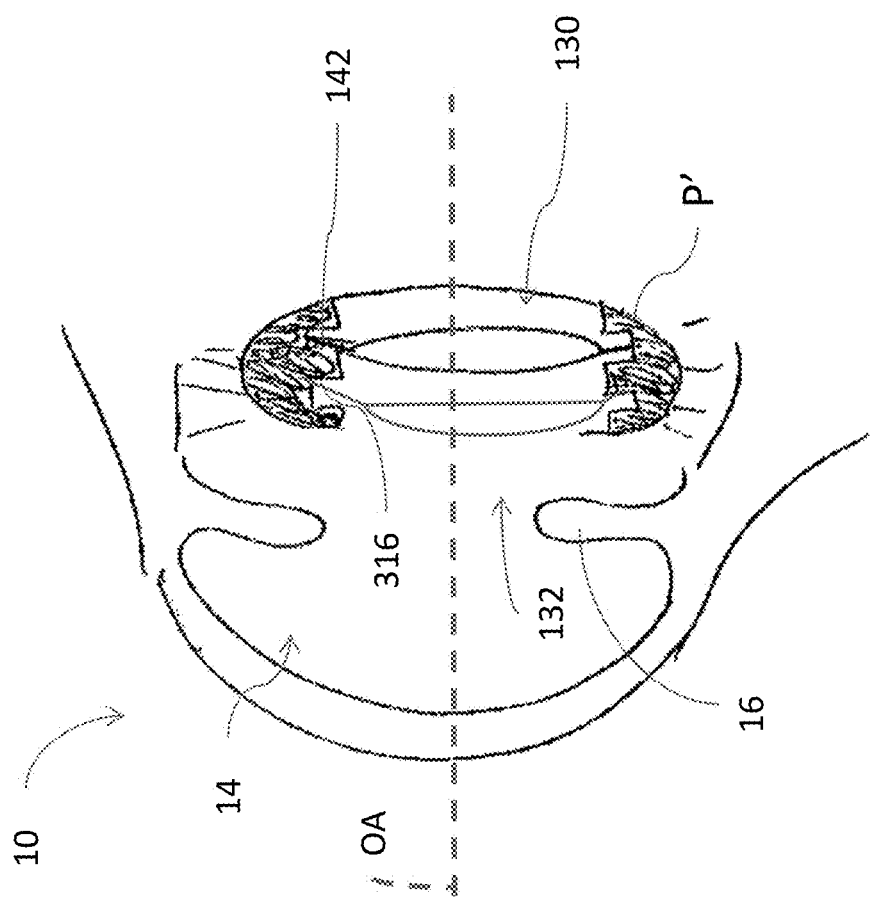
FIG. 8 is a cross-sectional view illustrating one embodiment of a method of using a piggyback IOL fixed in an existing posterior chamber IOL.

V. Bonding of the Piggyback IOL in the Capsular Bag or Other Natural Lens Structure FIG. 8 illustrates another method in which a second optic 132 is placed in the platform P' that has been formed in the lens capsule as discussed above. It can be that a patient's optical deficiency is not corrected by the optic 130. In some cases, the optic 130 was properly selected and placed for the patient at the time of initial placement but due to changes in the eye of the patient the optic 130 no longer provides appropriate correction. It can be that the optic 130 was properly selected based on information obtained pre-operatively but that the optic 130 did not perform as expected. Sub-optimal performance can be discovered even during the procedure using intra-operative aberrometry and other pseudophakic diagnostics. For these and other reasons the second optic 132 can be placed in the platform P' that is formed in the natural lens capsule as discussed above.

The second optic 132 can be provided with optics that cancel any aberrations that arise in the patient due to an advancing condition or that arise due to unexpected sub-optimal performance of the optic 130.

As in the optic 130, the optic 132 can be secured in the platform P' using a retention mechanism 142. The retention mechanism 142 of the second optic 132 can include a detent or other protrusion that engages a portion of one of the notches 316. In some embodiments, the second optic 132 can be secured using photobonding or another adherent.

VI. Further Methods

The foregoing embodiments can be used in a method of addressing vision problems by implanting the multi-piece IOL assembly 100 using various methods.

FIG. 1 shows the eye with another lens disposed therein. In one variation, the anterior chamber 14 of the eye 10 is accessed. This can be done by conventional methods. The natural lens is removed from the eye 10 preferably leaving the capsular bag 18 intact. For example, a capsulorhexis can be formed and the contents of the capsular bag 18 removed using phaco-emulsification. In some techniques a more precise approach is used. For example, a laser can be used to segment the natural lens allowing for the removal of specific parts of the natural lens. This second approach also can leave the capsular bag 18 intact for placement of the platform 104.

After the capsular bag has been prepared the platform 104 is advanced into the anterior chamber 14. The platform 104 and other components of the IOL assembly 100 can include elastic compression to inject through a small incision, e.g., through an incision of about 2.75 mm to 3.2 mm. Following injection, components of the multi-piece IOL assembly 100 can elastically expand. Thereafter the multi-piece IOL assembly 100 can be assembled in the eye. For example, upon release from the injector apparatus, the outer periphery 108 and the inner periphery 112 of the platform 104 expand to an uncompressed state. The platform 104 can be moved into engagement with an inner periphery of the eye such that the inner zone 116 of the platform 104 is centered on the optical axis OA. FIGS. 5 and 5A shows that the platform 104 can be moved into engagement with the interior surface of the capsular bag 18. The platform 104 can be moved into engagement with the sulcus S in other methods.

The platform is coupled with the sulcus S, the inside surface of the capsular bag 18 or with another inner periphery of the eye 10. Many different methods could be used for such coupling of the platform 104 with the inner periphery of the eye 10. As discussed above, the interface 119 between the outer surface 118 and the inner periphery of the eye 10 can be secured by laser fusion, photocuring, or another form of photobonding. Laser fusion can advantageously be performed at least in part by emitting light from a location outside the eye onto the zone where the interface 119 is to be formed. In at least this respect, laser fusion and other forms of photobonding are among the less invasive approaches to couple the platform 104 to the inner periphery of the eye 10. The interface 119 between the outer surface 118 and the inner periphery of the eye 10 can be secured by chemical gluing. Chemical gluing is advantageous in not requiring a light source to be directed into the eye. This can enhance safety in not requiring high energy light to be directed into the eye and also eliminates the need for this equipment when it is not otherwise in the operating room. Chemical bonding may require a cannula to deliver a chemical adhesive into the eye in a controlled manner. The interface 119 between the outer surface 118 and the inner periphery of the eye 10 can be secured by providing an adherent on the outer surface 118 of the platform 104. Providing an adherent on the outer surface 118 is advantageous in not requiring delivery of any adhesive into the eye via a cannula. An adherent may provide great security immediately upon placement.

After the platform 104 is coupled with the inner periphery of the eye 10, the optic 130 can be advanced into the anterior chamber of the eye. The optic 130 can be elastically compressed in an injector apparatus. The optic 130 can be inserted in the same injector apparatus as the platform 104. The optic 130 and the platform 104 can be injected sequentially without removing the tip of the injector apparatus from the anterior chamber 14.

After the optic 130 has regained an uncompressed state, the optic 130 can be coupled with the platform 104. The optical zone 134 of the optic 130 can be positioned in the inner zone 116 of the platform 104. In one technique, the outer periphery 138 is inserted into one of the slot 124, the slot 125, and the slot 126. In some methods, optical measurements can be used to determine into which of the slots 124, 125, 126 the optic 130 should be inserted. In one approach an aberrometry technique is used to determine the aphakic power of the eye 10. The aphakic power combined with the relative positions of the slots 124, 125, 126, the shape of the eye 10 and other factors can determine which of the slots 124, 125, 126 would provide the best refractive outcome. Thereafter the optic 130 can be placed in the slot that is chosen.

Advantageously the connection between the optic 130 and the platform 104 can be secured but releasable. For example, as discussed above the connection can be similar to a detent mechanism. Accordingly, in some techniques, a pseudophakic aberrometric measurement (with the optic 130 in place) can be made to confirm that the selected position provides the refractive result desired. If the result is not as desired, an action can be taken such as moving the optic 130 to a slot that is anterior or posterior of the initially selected and aberrometrically tested slot. Or, the second optic 132 can be placed in a more anteriorly located slot as discussed further below.

The manner of connecting the optic 130 to the platform 104 can include moving the outer periphery 138 of the optic 130 into one of the slots, e.g., into the slot 124. As the outer periphery 138 of the optic 130 is advanced to the location 146 of the platform 104 between the outer periphery 108 and the inner periphery 112 the optical zone 134 of the optic 130 comes to reset in the inner zone 116 of the platform 104. This position surrounds the optical axis OA of the eye and the multi-piece IOL assembly 100.

FIG. 5A shows another embodiment of an optic 130A in which resilient haptics 138A are coupled with a periphery of the optical zone 134. The haptics 138A can be inserted into one of the slots 124, 125, 126 to secure the optic 130A in the platform 104. The optic 130A can have more traditional haptic structures which may be more familiar to some surgeons or may be the only retention mechanism available for certain optics. The platform 104 and the platform P' are advantageous in that they are able to mate with the retention mechanism 142 and with other more conventional haptics as needed.

The multi-piece IOL assembly 100 can be assembled within the eye in several ways. They individual components can be completely separate prior to assembly and can thereafter be assembled in the eye using instruments. The platform 104 and the optic 130 and in some cases secondary lenses such as the second optic 132 can be inserted using the same inserter system to reduce, e.g., to minimize, the number of times the surgeon enters the eye. In other embodiment, the platform 104, the optic 130, and if present additional lenses such as the second optic 132, can be semi-assembled during insertion so that they can be inserted at once. Once in place, these components can be fixed together by pulling on strings that couple the components together after implantation.

The above presents a description of systems and methods contemplated for carrying out the concepts disclosed herein, and of the manner and process of making and using it, in such full, clear, concise, and exact terms as to enable any person skilled in the art to which it pertains to make and use this invention. The systems and methods disclosed herein, however, are susceptible to modifications and alternate constructions from that discussed above which are within the scope of the present disclosure. Consequently, it is not the intention to limit this disclosure to the particular embodiments disclosed. On the contrary, the intention is to cover modifications and alternate constructions coming within the spirit and scope of the disclosure as generally expressed by the following claims, which particularly point out and distinctly claim the subject matter of embodiments disclosed herein.

Although embodiments have been described and pictured in an exemplary form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

What is claimed is:

1. A multi-piece IOL assembly, comprising:
a platform comprising an outer periphery configured to at least partially directly engage with an inner periphery of an eye and an inner periphery surrounding an inner zone of the platform;
an optic comprising an optical zone, an outer periphery and a retention mechanism disposed on the outer periphery;
wherein the optic is configured to be disposed in the inner zone of the platform and to extend to a location between the inner periphery and the outer periphery of the platform to be secured to the platform at the location;
wherein the platform comprises an annular member having an outer surface, an anterior surface, a posterior surface and at least two slots enclosed at radially outward portions thereof by the outer surface; each of the at least two slots positioned at an anterior location relative to another of the at least two slots, and each slot corresponding to a change in power of the eye by moving the optic from one of the slots to another of the slots; and wherein each of the at least two slots are spaced apart.

2. The multi-piece IOL of claim 1, wherein the platform and the optic comprise different transmittance characteristics.

3. The multi-piece IOL of claim 2, wherein the platform is opaque.

4. The multi-piece IOL of claim 3, wherein the platform prevents transmission of substantially all incident light.

5. The multi-piece IOL of claim 2, wherein the optic is configured to prevent transmission of light outside the spectrum visible to humans.

6. The multi-piece IOL of claim 2, wherein the optic comprises variation in transmittance from a central zone to a peripheral zone, the central zone overlapping a central portion of the inner zone of the platform and the peripheral zone being adjacent to the inner periphery when the optic is coupled with the platform.

7. The multi-piece IOL of claim 1, where in the optic comprises a first optic and a second optic; wherein the first optic occupies a different slot of the two or more slots than the second optic.

8. The multi-piece IOL of claim 7, where at least one of the first optic and the second optic are moveable transverse to the optical axes thereof after being engaged with the platform to adjust the power of the multi-piece IOL within the eye.

9. The multi-piece IOL of claim 1, wherein one slot can be used for initial vision correction and another slot can be used for an adjustment procedure.

10. The multi-piece IOL of claim 1, wherein a mid-position slot is designated for initial placement of the optic and anterior and posterior slots are designated for adjustment placement to correct errors by effectively increase or decreasing the power of the eye compared to the power when the optic placed in the mid-position slot.

11. The multi-piece IOL of claim 9, further comprising a second optic configured to focus light away from a foveal region of the eye to a peripheral retinal location that is sufficiently sensitive to provide an image to a patient.

12. The multi-piece IOL of claim 9, further comprising a second optic configured to provide a substitute for natural accommodation by providing multifocality, enhanced or adjustable depth of focus.

13. The multi-piece IOL of claim 9, further comprising a second optic configured to correct power errors.

14. The multi-piece IOL of claim 9, further comprising a second optic configured to correct optical aberrations.

15. The multi-piece IOL of claim 1, wherein the at least two slots provide for displacement and fixation of the optic to control lens positioning within an eye to reduce one or more of tilt aberration, decentration aberration and pseudophakic power estimation error.

16. The multi-piece IOL of claim 1, wherein the platform comprises anatomy indicia on an anterior surface thereof, the anatomy indicia configured to align the platform to ocular anatomy.

17. The multi-piece IOL of claim 1, wherein the platform comprises an optic indicia on an anterior surface thereof and the optic indicia configured to rotationally align the optic within the eye to align an asymmetric power profile of the optic to the anatomy.

18. The multi-piece IOL of claim 17, wherein the optic indicia is a first optic indicia, the platform further comprising a second optic indicia, the first optic indicia configured to be rotationally align to the second optic indicia to cause the optic to be rotationally positioned within the eye to align an asymmetric power profile of the optic to the anatomy.

19. The multi-piece IOL of claim 1, wherein the outer periphery of the platform is configured to provide 360 degree contact with the anatomy to which the platform is coupled to reduce, minimize or eliminate cell migration between the platform and the anatomy.

20. The multi-piece IOL of claim 1, wherein the platform comprises three slots aligned in an anterior-posterior direction.

21. The multi-piece IOL of claim 1, wherein the platform comprise an aperture disposed on the anterior surface configured to receive an instrument for rotationally positioning the platform in the eye.

22. The multi-piece IOL of claim 1, wherein the platform is configured to be supported in an interior of a capsular bag of an eye.

23. The multi-piece IOL of claim 1, wherein the platform comprises one or more haptics disposed at the outer periphery.

24. The multi-piece IOL of claim 1, wherein the platform is configured to be supported in a sulcus of an eye.

* * * * *